United States Patent [19]

Angermann et al.

[11] Patent Number: 4,689,838
[45] Date of Patent: Sep. 1, 1987

[54] GOGGLES WITH INTERCHANGEABLE LENSES

[75] Inventors: Gottfried Angermann, Neuhofen; Berthold Hiebl, Traun, both of Austria

[73] Assignee: Optyl Eyewear Fashion International Corporation, Norwood, N.J.

[21] Appl. No.: 831,408

[22] Filed: Feb. 20, 1986

[30] Foreign Application Priority Data

Feb. 21, 1985 [DE] Fed. Rep. of Germany ....... 3506079

[51] Int. Cl.$^4$ .............................................. A61F 9/02
[52] U.S. Cl. ............................................ 2/441; 2/436
[58] Field of Search ................... 2/441, 443, 440, 439, 2/426, 428, 429, 430, 432, 436, 452, 435

[56] References Cited

U.S. PATENT DOCUMENTS

| | | | |
|---|---|---|---|
| 2,907,041 | 10/1959 | Finn | 2/432 |
| 3,363,262 | 1/1968 | Lindblom | 2/441 |
| 3,718,937 | 3/1973 | Smith | 2/436 |
| 3,945,044 | 3/1976 | McGee et al. | 2/436 |
| 4,056,853 | 11/1977 | Bottazzini et al. | 2/443 |
| 4,149,276 | 4/1979 | Castro | 2/441 X |

*Primary Examiner*—Peter Nerbun
*Attorney, Agent, or Firm*—Fitch, Even, Tabin & Flannery

[57] ABSTRACT

Goggles having a flexible frame deformable to conform to and seal about the wearer's face and eyes. A strap secured to the goggles adjacent the temples secures the goggles to the wearer's head. A rigid frame is secured to the periphery of the flexible frame, the rigid frame having a channel adjacent the upper and lower edges of the flexible frame which is adjacent the temple area. Lenses including a peripheral flange receivable within the channel of the rigid frame are slidable within the channel to locate each lens with respect to the rigid frame. A rigid handle or grip is secured to the temple portion of the lens to close the open end of the channel and to lock the lens to the flexible frame.

5 Claims, 6 Drawing Figures

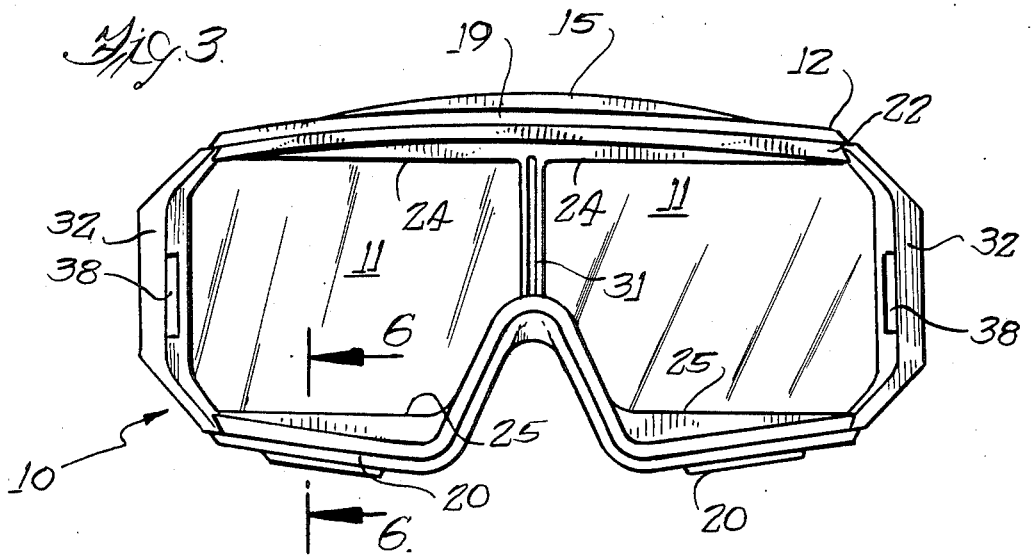
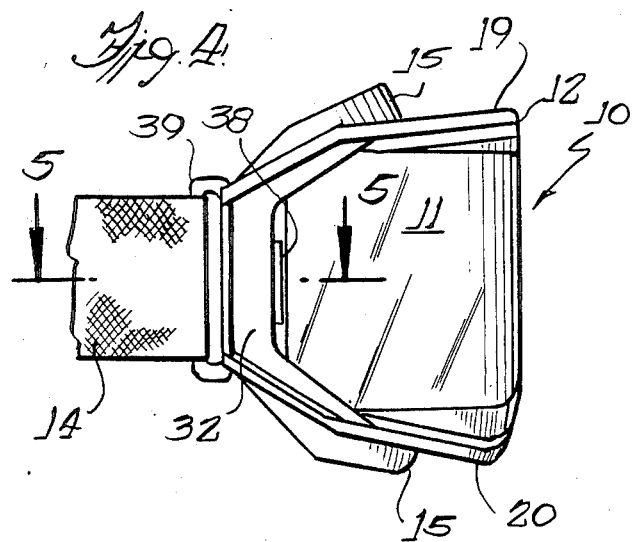
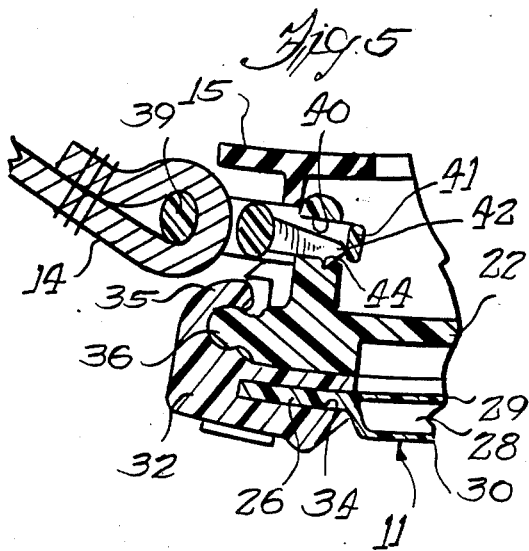
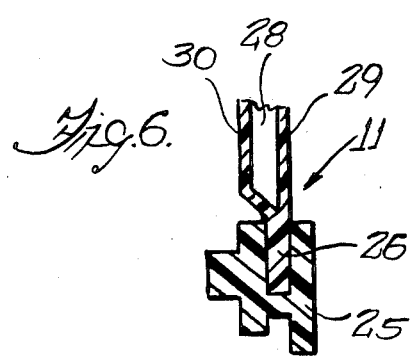

GOGGLES WITH INTERCHANGEABLE LENSES

The present invention relates to goggles for skiing and the like and, more particularly, to an improved interchangeable lens system for goggles.

There are many activities such as snow skiing or driving open-cockpit cars or motorcycles which, for reasons of both comfort and safety, require the participant to utilize some form of eye protection. Not only does the eyewear prevent objects from lodging in the eye, but also prevents the surface of the eye itself from drying out, which would cause excessive blinking or tearing and, consequently, reduce visual acuity, a serious drawback when quick reactions are needed while one is skiing or driving. Further, if the eyewear is provided with the proper colored lens, eyestrain due to glare can be greatly reduced and, in fact, visual acuity can be increased in comparison to the naked or uncorrected eye. Indeed, it is known that under flat light conditions yellow colored lenses help to bring out otherwise imperceptible contrasts in the depth or contours of the terrain.

There have been numerous attempts to provide goggles adaptable for snow skiing with interchangeable lenses of different colors to provide the optimal vision, despite the often variable atmospheric and light conditions that may be encountered by a skier in the course of even a single day. On some goggles of this type, the lenses are interchangeable only with the use of special tools by a trained professional. Other such goggles include a flexible frame that must be deformed in order to remove and insert the different lenses. While it is possible to change such lenses while one's fingers are warm and manual dexterity is great, such is generally not the case when one is on the ski slopes. Fingers are often numb or clad in gloves or mittens, reducing manual dexterity to a minimum and making the changing of lenses in the goggles extremely difficult. Further, when such lenses are not properly mounted in the goggles body, the lens may pop out at the most inopportune times, resulting in possible loss of the lens and, even worse, direct or indirect injury to the wearer. That is, the lens itself might injure the wearer, or the loss could adversely affect the wearer's vision so as to precipitate an accident or injury.

Accordingly, it is the principle object of the present invention to provide goggles with an improved interchangeable lens system.

More particularly, it is an object to provide goggles in which lenses are easily interchangeable with a minimum amount of manual dexterity under adverse environmental conditions.

An additional object is to provide such goggles in which the lenses positively interlock with the goggles to prevent unintended separation thereof.

These objects, and others which will become apparent upon reference to the following detailed description and accompanying drawing, are provided by goggles having a flexible frame deformable to conform to and seal about the wearer's face and eyes. A strap secured to the goggles adjacent the temples secures the goggles to the wearer's head. A rigid frame is secured to the periphery of the flexible frame, the rigid frame having a channel adjacent the upper and lower edges of the flexible frame which are open adjacent the temple area. Lenses including a peripheral flange are insertable in the opening in the channels of the rigid frame adjacent the temples and are slidable within the channels to locate the lenses with respect to the rigid frame. A rigid grip or handle is secured to the temple portion of each lens which is operable to close the open end of the channel and to lock the lens to the rigid frame so as to removably secure the lens within the channel.

BRIEF DESCRIPTION OF THE DRAWINGS

FIG. 3 is a front elevation of the goggles of FIG. 1;

FIG. 4 is a side elevation of the goggles of FIG. 1;

FIG. 5 is a an enlarged cross-sectional view, taken substantially along line 5—5 of FIG. 4, showing the interlocking structure of the removable lenses and the rigid frame; and FIG. 6 is an enlarged cross-sectional view taken substantially along line 6—6 of FIG. 3, showing the channel of the rigid frame member.

DETAILED DESCRIPTION OF THE PREFERRED EMBODIMENT

Figure 1:
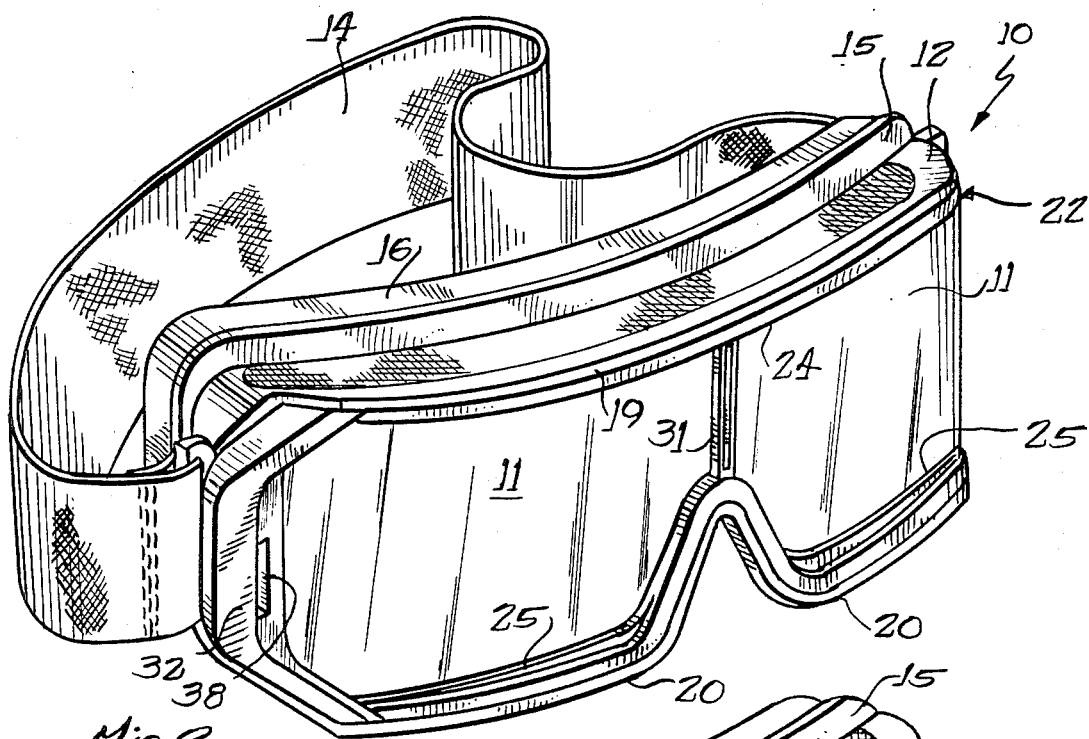
FIG. 1 is a perspective view of a pair of goggles according to the present invention.
Figure 2:
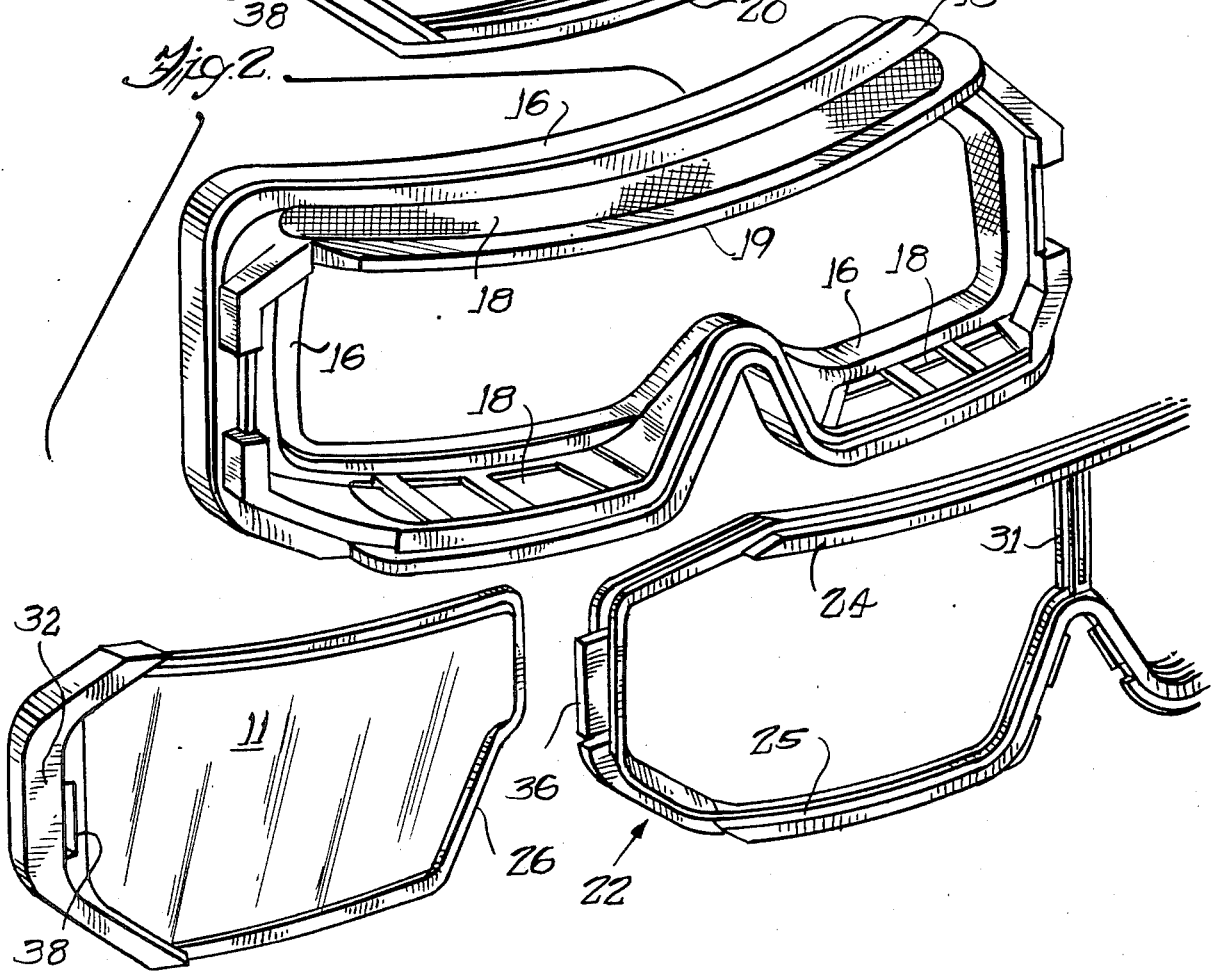
FIG. 2 is an exploded perspective view of the goggles of FIG. 1.

Turning to the figures of the drawing, which are for purposes of illustration and not limitation, there is seen in FIG. 1 a perspective view of a pair of goggles 10 embodying the present invention. The goggles 10 include lenses 11 held in a frame portion, generally indicated by 12, and secured to the wearer's head by means of an elasticized strap or band 14 that is attached to the frame portion 12 and is adjustable in length to suit the individual wearer.

The frame portion 12 includes a flexible or pliable main frame 15 that includes a foam rubber material 16 on the portion that contacts the wearer's face so as to comfortably conform over the eyes and about the nose and provide a seal with the wearer's face to prevent the ingress of, e.g., snowflakes, into the interior portion of the goggles 10. The pliable main frame 15 may include vents defined by openings 18 in the upper and lower surfaces 19 and 20 of the main frame 15. The vents 18 serve to allow circulation of ambient air about the lenses so as to minimize the fogging of the lenses and are covered with, e.g., a porous foam 21 that allows air to pass through, but not snowflakes.

In keeping with the invention, the goggles 10 include a rigid frame member 22 secured to the pliable main frame 15 for slidably receiving and securely holding the lenses 11. The frame member 22 is molded in one piece and bounds the open front of the main frame. The rigid frame 22 includes two approximately U-shaped tracks (as seen in FIG. 3) open or having a discontinuity at the temples for receiving the lenses 11, upper and lower channels 24, 25, respectively, adjacent the upper and lower portions 19, 20 of the main frame 15. The channels 24, 25 are generally parallel and have a generally U-shaped cross-section (best seen in FIG. 6) sized to receive a flange portion 26 coextensive with the outer edges of each lens 11. (As seen in FIG. 6, the lenses 11 may be of the insulated type, having an air pocket 28 bounded by inner and outer lens surfaces 29 and 30, respectively.) To maintain the channels 24, 25 in proper spaced relationship and to further rigidify the frame 22, a crossbar 31 overlying the bridge of the wearer's nose connects the upper and lower channels 22, 24. The crossbar 31 has a cross-section similar to that of the channels 24, 25, so as to receive the flange portion 26 of each lens and to effectively form a seal between the lenses 11 and the frame 22.

To ensure that the lenses 11 are secured to the goggles 10 when properly located in the channels 24, 25 of the rigid frame 22, each lens 11 includes a rigid grip or handle member 32 secured to the temple portion of each lens 11. The handle 11 is formed to complement the generally U-shaped configuration of each lens track so as to close the open end thereof. As best seen in FIG. 5, the handle 32 includes a slot 34 which receives the flange 26 of the lens 11, the handle 32 being, e.g., glued thereto. The handle 32 also includes a clip portion 35 that mates with the projecting bead portion 36 formed in the temple portion of the rigid frame member 22. When the lenses 11 are fully inserted into their respective tracks, the clip portions 35 of each handle snaps over the bead 36 on the rigid frame 22 to securely and positively hold each lens 11 in place within its slot and prevent unintended removal of the lens 11. Each handle 32 includes an indentation 38 to facilitate gripping the handle for inserting or removing the associated lens 11 from the track.

As best seen in FIG. 5, the elasticized band 14 is secured to the temple portions of the goggles 10 by means of rigid loops or brackets 39 that extend through a slot 40 in the rigid frame member 22. Each bracket 39 includes a U-shaped tongue 41 having an open interior. The tongue 41 fits through the slot 40 to locate the loop 39, while a detenting finger 42 secured to the loop 39 interior of the tongue 41 mates with a shoulder 44 on the interior of the slot 40 to lock the bracket 39 in place.

An assortment of different-colored lens pairs may be carried by the wearer so that the proper lenses may be selected and inserted into the rigid frame 22 for the various light conditions. To insert the lenses 11, the wearer simply aligns the flanges 26 with the tracks 24, 25 and slides the lens along the track until the clip 35 on the handle 32 mates with the projecting bead 36 on the rigid frame 22 to secure the lens in place. To remove the lens, the handle member 32 is simply pushed in the opposite direction to release the clip 35 on the handle portion 32 from the projecting bead 36.

Thus, a goggles system has been provided that permits the easy changing of lenses to suit various light conditions, while affording positive locking of the lenses in place. While the invention has been described in terms of a preferred embodiment, there is no intent to limit it to the same, on the contrarv, it is intended to cover all modifications and equivalents within the scope of the appended claims.

What is claimed is:

1. Goggles comprising flexible frame means deformable to conform to and seal about the wearer's face and eyes; strap means secured to the goggles adjacent the temple for securing the goggles to the wearer's head; rigid frame means secured to the periphery of the flexible frame means and having a beaded edge, and a channel means adjacent the upper and lower edges of the flexible frame means, the channel means having an opening adjacent the temple area of the flexible frame means; removable lens means including a peripheral flange receivable within the opening of the channel means so that the lens means are slidable within the channel means to locate the lens means with respect to the rigid frame means; and rigid gripping means secured to the temple portion of the lens means operable to close the opening of the channel means and including locking clip means which snaps over the beaded edge of the rigid frame means to removably secure the lens means within the channel means.

2. The combination of claim 1 including channeled crossbar means aligned with the bridge of the nose securing the channel means adjacent the upper edge of the flexible frame means to the channel means adjacent the lower edge of the flexible frame means, and the lens means comprises two separate lenses, each insertable into the channel adjacent each temple.

3. The combination of claim 1 wherein the rigid grip means includes a depression to provide a finger hold to facilitate insertion and removal of the lens means.

4. The combination of claim 1 wherein the strap means are secured to the goggles by bracket means having a tongue received in a slot in the rigid frame means, the tongue including a detenting finger that secures the bracket to the rigid frame.

5. The combination of claim 2 wherein one said beaded edge is located adjacent each temple area of the rigid frame means.

* * * * *